United States Patent [19]
Kimura

[11] Patent Number: 5,396,104
[45] Date of Patent: Mar. 7, 1995

[54] RESIN COATED BONDING WIRE, METHOD OF MANUFACTURING THE SAME, AND SEMICONDUCTOR DEVICE

[75] Inventor: Masao Kimura, Kawasaki, Japan
[73] Assignee: Nippon Steel Corporation, Japan
[21] Appl. No.: 613,700
[22] PCT Filed: Mar. 27, 1990
[86] PCT No.: PCT/JP90/00405
 § 371 Date: Nov. 19, 1990
 § 102(e) Date: Nov. 19, 1990
[87] PCT Pub. No.: WO90/11617
 PCT Pub. Date: Oct. 4, 1990

[30] Foreign Application Priority Data
Mar. 28, 1989 [JP] Japan .................... 1-75794
Apr. 26, 1989 [JP] Japan .................... 1-107067

[51] Int. Cl.⁶ .................... H01L 23/28; H01B 7/00
[52] U.S. Cl. .................... 257/784; 257/792; 174/110 SR; 174/110 N; 428/458
[58] Field of Search .................... 357/72, 74; 257/784, 257/788, 792; 174/110 SR, 110 N; 428/458

[56] References Cited

U.S. PATENT DOCUMENTS

| | | |
|---|---|---|
| 4,486,945 | 12/1984 | Aigoo .................... 357/72 |
| 4,488,674 | 12/1984 | Egawa et al. .................... 228/179 |
| 4,497,849 | 2/1985 | Hughes et al. .................... 427/120 |
| 4,678,114 | 7/1987 | Egawa et al. .................... 228/176 |
| 4,821,148 | 4/1989 | Kobayashi et al. .................... 357/72 |
| 4,926,238 | 5/1990 | Mukai et al. .................... 357/72 |

FOREIGN PATENT DOCUMENTS

| | | |
|---|---|---|
| 0110635 | 6/1984 | European Pat. Off. . |
| 2221488 | 10/1974 | France . |
| 0067360 | 5/1980 | Japan . |
| 58-3239 | 1/1983 | Japan . |
| 58-63142 | 4/1983 | Japan . |
| 0154054 | 9/1984 | Japan . |
| 0224237 | 11/1985 | Japan . |
| 61-186239 | 9/1986 | Japan . |
| 0034960 | 2/1990 | Japan . |

*Primary Examiner*—Rolf Hille
*Assistant Examiner*—David Ostrowski
*Attorney, Agent, or Firm*—Pollock, Vande Sande & Priddy

[57] ABSTRACT

Disclosed are an insulation film covered bonding wire comprising a conductive metal core wire the circumference of which is coated with an insulation film of an at least one type composed of polymer resin materials selected from a group of aromatic polyesters, polyimides, polyether-ether ketones, polyamides, polysulfones, and liquid crystal polymers, wherein no crack is developed to the insulation film when an impact force of 1 cm.g is applied to the coated wire by a drop weight, a method of manufacturing the bonding wire, and a semiconductor device using the same.

6 Claims, 3 Drawing Sheets

RESIN COATED BONDING WIRE, METHOD OF MANUFACTURING THE SAME, AND SEMICONDUCTOR DEVICE

TECHNICAL FIELD

The present invention relates toga bonding wire, a method of manufacturing the same and a semiconductor device using the wire.

BACKGROUND ART

A bonding wire used in a manufacturing process of semiconductor devices has been composed of a conductive metal core wire material of, for example, gold (Au), copper (Cu), aluminum (Al) and the like in the form of a bare wire.

Therefore, when bonding pads of a semiconductor pellet are bounded to conductors to external output terminals such as inner leads of a lead frame using such wires, a problem of short-circuiting arises in such a case that a wire comes into contact with another wire, an inner lead, a tab or the like due to any reason such as poor bonding, resin flow in a resin mold type package or the like.

In particular, as a distance between a pellet and inner leads is increased in correspondence to the increase in the number of pins in a large scale integrated circuit (LSI), a length of a wire span must be increased. In this case, however, short-circuiting, faulty chip edges and mount touches and the like are more liable to be caused by a wire which is curled and comes into contact with an adjacent wire.

Consequently, it has been proposed to coat a bonding wire with an insulation film. For example, U.S. patent application Ser. No. 4,488,674 proposes to coat a bonding wire with a polymer resin material which has an insulating property and is thermally decomposed at a temperature of 200° to 300° C. and volatilized to prevent short-circuiting and the like. However, it is difficult to obtain resins having such properties, and further in a case of polyethylene terephthalate, a continuous bonding cannot be carried out due to wire break caused when a second bond is subjected to contact bonding, because it is a relatively brittle crystalline material, or in a case of polycarbonate, a bonding wire obtained after it has been coated with a film is naturally curled and thus it is difficult to process it by a high speed bonding machine and keep the positional accuracy thereof when it is processed at a high speed. As a result, at present, these materials are not practically used because of such a drawback that the workability of a bonding process is deteriorated, and the like.

Further, a new problem in practical use arises in that some of polymer resin materials used for coating a bonding wire is left between the bonding wire and a lead frame or bonding pads of a semiconductor pellet, or a piece of the coated resin broken by an impact produced when bonding is carried out cuts the bonding wire of gold or the like or injures it to cause wire cutting-off.

In general, a heat resistant insulation coating material includes resins called engineering plastics, and among them aromatic polyester has been found to be excellent in these characteristics [for example, Japanese Patent Kokai (Laid-Open) Nos. Sho 54-138056 and Sho 58-137905].

Nevertheless, generally known aromatic polyester resins are excellent in heat resistance, wear resistance, fire retardance, mechanical characteristics such as tensile strength and the like, impact resistance, and electric characteristics such as insulating property and the like, but it is poor in an extrusion processing property, and thus it has been very difficult to form a thin insulation film of uniform thickness on the circumference of a bonding wire by an electric wire coating method using an extruder. In addition, aromatic polyester resins whose extrusion processing property has been improved by modification or the like have a problem in that they have poor heat and wear resistances.

Further, there has been employed a method by which a resin material is dissolved in a proper solvent and coated to form an insulation film of uniform thickness on the circumference of a bonding wire. Since, however, aromatic polyester resins having high mechanical strength and heat resistance have high chemical resistance, a suitable solvent for it is not available and then it has been difficult to uniformly form a thin coating film on a bonding wire.

Further, when the aromatic resins are made to be easily dissolved in solvent by modification or the like, they are usually deteriorated in weather resistance, heat resistance and the like. Therefore, it has been very difficult to make an insulation bonding wire using aromatic polyester as a coating layer.

Further, when heat resistant thermosetting resins are used, there is a drawback in that carbides and the like of the resins are left in the under portion of balls even after they have been formed or the resins are not separated properly from metal in a bonding process of a bonding wire with a lead frame and thus the bonding strength thereof is greatly lowered.

Although Japanese Patent Applications Kokai Nos. Sho 60-224255 and Sho 62-30359 disclose that a copper wire having an oxide insulation coating film is used as a bonding wire, it is not yet practically used, because the removal of the oxide coating film in a bonding process and a continuous bonding of the wire are difficult.

Further, there is a trial to coat the surface of a bonding wire with another material and, for example, Japanese Patent Application Kokai No. Sho 62-97360 discloses to form precious or corrosion resistant metal on a copper electrode thin wire. A purpose of this case, however, is to prevent surface oxidation and not to solve the above problems.

Further, when such a resin coated insulation bonding wire is manufactured, polymer materials generally excellent in an insulating property are also excellent in heat resistance, wear resistance, fire retardance, mechanical characteristics such as tensile strength and the like, impact resistance, and electric characteristics such as insulation property and the like, but they are poor in an extrusion processing property. Therefore, it is very difficult to form a thin insulation film of uniform thickness on the circumference of a bonding wire by an electric wire coating method using an extruder.

To cope with this problem, there is a device to form an insulation coating film while bonding is carried out, and as an example thereof there is a method of supplying a sticky liquid insulation agent through a guide portion of a capillary tube, as disclosed in Japanese Patent Application Kokai No. Sho 52-79657.

This method, however, is difficult to smoothly supply the insulation agent, and further, as shown in Japanese Patent Kokai No. Sho 61-269319, a method of forming an insulation coating film by spraying an insulation material onto a bonding wire after it has been stretched, and the like cannot form a uniform coating film. Thus, these methods are not practical in the formation of a uniform thin insulation coating film on a bonding wire.

DISCLOSURE OF THE INVENTION

An object of the present invention is to solve the above problems of prior art and provide a resin coated bonding wire capable of preventing short-circuiting caused when bonding wires come into contact each other or a bonding wire comes into contact with other conductor parts, a method of manufacturing the bonding wire, and a semi-conductor device using it.

The present invention relates to a bonding wire composed of a conductive metal core wire coated with an insulation film of a polymer material and a method of manufacturing the same, the polymer material having such a property that when an impact force of 1 cm.g is applied thereto using a falling weight, no crack is developed to the insulation film. Since the bonding wire according to the present invention is not only excellent in a bonding property but also has a predetermined strength, it can be continuously bonded without being cut off.

Further, the present invention relates to a semi-conductor device in which bonding pads of a semi-conductor pellet are bonded and electrically connected to conductors to external output terminals using the above bonding wire.

Figure 1:
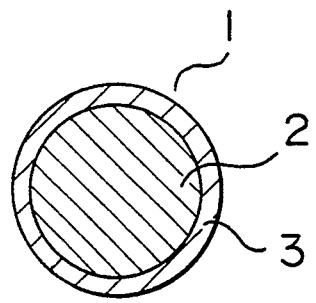
FIG. 1 is a cross sectional view of a bonding wire according to the present invention.

The numerals in the figures show the following parts, portions, units and the like.

1 . . . bonding wire, 2 . . . metal core wire, 3 . . . insulation film, 4 . . . wire bonding surface, 5 . . . package base, 6 . . . cavity, 7 . . . semi-conductor pellet, 8 . . . lead frame, 9 . . . low melting point glass, 10 . . . cap, 11 . . . bonding wire, 12 . . . feed spool, 13 . . . tension control unit, 14 . . . cleaning unit, 15 . . . resin coating unit, 16 . . . take-up spool, 17, 17' . . . drying furnace, 18 . . . guide roller.

BEST MODE OF CARRYING OUT THE PRESENT INVENTION

As a result of an intensive study of the causes by which resin coated bonding wires are cut off or poorly bonded, the inventors have found that the wires are poorly bonded because resin is left between the bonding wire and a lead frame and bonding pads when they are bonded, and the wires are cut because a polymer material injures a metal core wire such as gold or the like when a coated film of the polymer material to which impact is applied is cracked or broken.

Therefore, the inventors have found that the impact characteristics required to a polymer material used as a coating film are not determined by the results of Izod impact test (JIS K 7110-1977), Charpy impact test (JIS K 7111-1977), a film breaking impact test [Matsumoto, plastics, 30, 11, 59 (1979)] and the like which are generally used as an impact test for polymer materials, but determined by the results of REA method (REA PE22, PE23) which is a typical impact test method for the outside casing of an electric wire, cable and the like, because the results of REA method obtained by applying an impact force of 1 cm.g to a bonding wire by a falling weight at a room temperature best correspond to the results of a continuous bonding test.

As a result various studies effected based on the above knowledge, it has been found that the bonding wire of the present invention is needed to satisfy that the wire is not cut off or no crack is developed to an insulation film when an impact force of 1 cm.g is applied thereto by a falling weight, and thus the present invention has been completed.

The above cutting-off can be determined by a visual observation, but the crack is not always easily determined by the visual observation, and thus it is preferable that it is observed using an optical microscope or a scanning electron microscope with magnification of hundreds, if possible.

As a thickness of an insulation film is increased, the strength thereof is naturally increased. However, a film thickness exceeding 10 μm is not suitable in view of the object of the insulation film to be used to a bonding wire, and thus it is needed that the insulation film in a range from 0.01 μm to 10 μm is not usually cracked by an impact force of 1 cm.g applied thereto when it is subjected to a strength test using a falling weight.

Further, when a bonding wire coated with the insulation film is applied to a semi-conductor device, the insulation film must withstand a high temperature of about 300° to 400° C., because the semiconductor device is required to have heat resistance withstanding such a temperature when it is in operation. On the other hand, since the bonding wire is bonded at a temperature from 150° to 250° C., the insulation film is required to have such a characteristic incompatible with the above that it is easily separated from the metal portion of the wire at the temperature.

As a result of various studies of resins capable of satisfying the above conditions, it has found that aromatic polyesters (polyarylates), polyimides, polyether-ether ketones, polyamides, polysulfones, polyether sulfones, liquid crystal polymers and mixtures thereof, which are excellent in heat resistance and balanced in mechanical strength such as impact resistance, are preferable.

The aromatic polyester resin according to the present invention is composed of an aromatic dihydroxy compound residue group and an aromatic dicarboxylic acid compound residue group and is a thermoplastic aromatic polyester which may be branched obtained by causing an aromatic dihydroxy compound to react with an aromatic dicarboxylic acid.

An example of the aromatic dihydroxy compounds includes 2,2-bis(4-hydroxyphenyl)propane (=bisphenol A), tetramethylbisphenol A, tetrabromobisphenol A, bis(4-hydroxyphenyl)-p-diisopropyl benzene, hydroquinone, resorcinol, 4,4'-dihydroxydiphenyl and the like, and the bisphenol A is particularly preferable.

The branched aromatic polyester resin can be obtained by using a polyhydroxy compound as a substitute for, for example, 0.1 to 2 mol % of the above dihydroxy compound such as a polyhydroxy compound such as, for example, phloroglucin, 4,6-dimethyl-2,4,6-tri(hydroxyphenyl) heptene-2, 4,6-dimethyl-2,4,6-tri(4-hydroxyphenyl) heptane, 2,6-dimethyl-2,4,6-tri(4-hydroxyphenyl) heptane-3, 4,6-dimethyl-2,4,6-tri(4-hydroxyphenyl) heptane, 1,3,5-tri(4-hydroxyphenyl) benzene and 1,1,1-tri(4-hydroxyphenyl) ethane, and 3,3-bis(4-hydroxyaryl) oxyindole (=isacin bisphenol), 5-chloroisatin, 5-bromoisatin, etc.

Further, m- and p-methyl phenol, m- and p-propyl phenol, p-bromophenol, p-tert-butylphenol, etc. are preferable as a monoaromatic hydroxy compound suitable for adjusting a molecular weight.

A typical aromatic polyester resin includes a bis(4-hydroxyphenyl) alkane dihydroxy compound, in particular a polyester mainly composed of bisphenol A, and also a polyester copolymer obtained by using at least two kinds of aromatic dihydroxy compounds together and branched polyester obtained by using a small amount of a triphenol compound together. In addition, a mixture of at least two kinds of aromatic polyester resins may be used.

The aromatic dicarboxylic acid includes terephthalic acid, isophthalic acid, naphthalene di-carboxylic acid, diphenyl dicarboxylic acid, methyl terephthalic acid, methyl isophthalic acid, diphenyl ether dicarboxylic acid, diphenyl sulfone dicarboxylic acid, diphenoxy ethane dicarboxylic acid, etc. Then lower alkylesters, acid halides thereof, etc. are preferably included in addition to the above free dicarboxylic acid. A part (e.g., 30 mol % or less) thereof may be substituted by aliphatic dicarboxylic acid such as succinic acid, adipic acid, sebacic acid etc. and a cyclic aliphatic dicarboxylic acid such as cylohexane dicarboxylic acid, and the like.

Among them, aromatic polyester synthesized from bisphenol A and (iso)terephthalic acid and having the following skeleton structure is most preferable from a view point of solvent solubility and heat resistance.

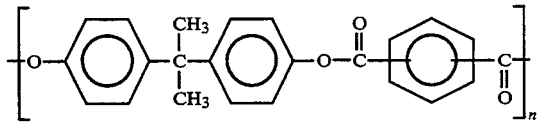

In particular, aromatic polyester among the mentioned above having a melt index of 1.0 to 100 g/10 min (temperature: 300° C., load: 2.160 kg) is most suitable, when it is tested in accordance with ASTM-D1238.

Although the reason why aromatic polyesters having a melt index within the above range are most suitable as an insulation film is not apparent, it is supposed that the coating film formed of the aromatic polyester used in the present invention has an amorphous high order structure, whereas polyethylene terephthalate and polybutylene terephthalate generally used as engineering plastics are crystalline.

When the above aromatic polyester has a melt index less than 1.0 g/10 min, the viscosity thereof is too high and thus a coating film layer of uniform thickness cannot be formed on a bonding wire. Even if the bonding wire is partially coated with the film of substantially uniform thickness, the wire has a poor continuous bonding property and lacks in reliability.

When the aromatic polyester has a melt index exceeding 100 g/10 min, the viscosity thereof is too low and thus the intimate adhering property thereof with a bonding wire is deteriorated and the polyester is liable to be exfoliated. In this case, although no problem arises in a continuous bonding property, an insulating property is lost. As a result, both the cases cannot provide a practically applicable coating film layer.

A thicker insulation film used in the insulation film coated bonding wire according to the present invention is more excellent in an insulating property, but at the same time worse in a bonding property. Further, a thinner insulation film is more excellent in a bonding property but has a deteriorated insulating performance, and when a thickness of the insulation film is 0.01 μm or less, it has deteriorated voltage resistance.

Consequently, a proper thickness of the insulation film is preferably 0.01 μm or more, more preferably 0.01 to 2 μm, and most preferably 0.02 to 1.0 μm.

Further, various additives such as an anti-oxidant, flame retardant, filler, voltage stabilizing agent, lubricant, auxiliary processing agent, UV absorbent, etc. which have been conventionally used for this type of resin materials may be added to this polymer resin material.

The coated bonding wire according to the present invention is preferably manufactured in such a manner that a bonding wire mounted on a feed spool is continuously fed into a coating liquid in which the above polymer resin material is dissolved, caused to pass through the liquid, drawn upward in the vertical direction to remove solvent therefrom to thereby form the bonding wire uniformly coated with the insulation resin, and then the thus obtained coated bonding wire is wound to a take-up spool.

Although a method of forming the coating film includes an extrusion coating method, electrostatic power coating method, spray coating method, electrode coating method and the like in addition to the above dipping coating method, the dipping coating method is preferably used to coat a wire with a very thin insulation film of uniform thickness as in the present invention.

A method of manufacturing the bonding wire according to the present invention will be described below in detail.

When an insulation coating film is to be formed on the surface of a bonding wire, the conductive bonding wire is sufficiently cleaned, then mounted on a feed spool, and continuously fed. Further, if necessary, it is cleaned by a solvent such as trichloroethylene, chloroform, etc. in a pretreatment bath or it is subjected to a surface treatment to improve an adhering property and the like of the bonding wire with resin and then, if necessary, it is caused to pass through a drying furnace to dry the surface thereof.

Next, the above bonding wire is caused to pass through a coating liquid prepared by dissolving resin and filtrating it to remove foreign substances therefrom, then drawn upward in the vertical direction, and caused to pass through a drying furnace, if necessary, to remove solvent to thereby form the bonding wire uniformly coated with the insulation resin, and then the thus obtained coated bonding wire is wound to a take-up spool, whereby the resin coated insulation bonding wire is continuously and effectively manufactured.

The drying furnace may be a multistage type and a drying temperature thereof is controlled to enable thin insulation coating film having a preferable surface property to be formed. Preferably, the resin coated bonding wire is subjected to an ultrasonic cleaning treatment to clean the surface thereof and an electro-static charge prevention treatment such as shower cleaning using ionized air or the like, and then re-wound by predetermined spools to a desired length.

Further, the bonding wire is preferably coated with the film while monitoring a tension applied thereto, and the cut-off of the bonding wire can be checked by applying a predetermined tension to the wire being coated with the film by a back tension controller.

Further, it is possible to prevent the wire from being expanded by an excessive tension applied thereto or from being out of a guide roller due to a too small tension applied thereto while the wire is coated with the film. The wire is preferably drawn upward in as vertically as possible, and if the wire is dried in the state it is deflected from the vertical direction by a large angle, the coated film is difficult to be formed on the circumference of the bonding wire to a uniform thickness.

The bonding wire as a base-member used in the present invention is mainly composed of gold, copper, and aluminum having good electric conductivity.

Further, the insulation resin used in the present invention includes the above polyesters, polyamides, polyacetals, polysulfones, polyether sulfones, polyether-ether ketones, etc. and derivatives and blends thereof.

The insulation coating film has a thickness of preferably 0.01 to 10 $\mu$m, more preferably 0.01 to 2 $\mu$m and most preferably 0.02 to 1.0 $\mu$m. When the thickness exceeds 10 $\mu$m, the film is poor in a bonding property, although it is excellent in an insulating property, and thus bonding wire cannot be continuously bonded or the bonding strength thereof is made smaller. In addition, when the thickness is less than 0.01 $\mu$m, the film is poor in the insulating property, although it is excellent in a bonding property, and thus a problem arises in practical use.

Although a resin concentration of the coating liquid can be arbitrarily selected depending upon the viscosity thereof, a thickness of a coating layer and the like, usually it is preferably 20 wt % or less and more preferably 10 wt % or less to form a uniform coating film.

The coating layer can be made to a multi-layer by disposing a coating apparatus provided with coating liquid in which the resin is dissolved in multistage. In this case, a thickness of the coating layer is preferably within the above-mentioned range.

Further, when the coating apparatus according to the present invention is disposed as a part of a wire drawing process, wire drawing and coating can be continuously carried out easily.

Solvents used to dissolve the resin is not particularly limited as long as it is so-called good solvent to the resin used, and, for example, when aromatic polyester is used, chloroform, trichloroethylene, etc. can be used and when polyamide is used, formic acid, m-cresol, etc. can be used.

The present invention will be described below in specific detail with reference to drawings.

FIG. 1 is a cross sectional view of a bonding wire according to the present invention.

The bonding wire 1 in FIG. 1 has a conductive metal core wire 2 having a circular cross section at the center thereof. The metal core wire 2 is made of a known conductive material composed of, for example, gold, copper, aluminum, alloys thereof, etc., and, for example, silicon (Si), magnesium (Mg) or manganese (Mn) is added to the aluminum.

The circumference of the metal core wire 2 is coated with an electric insulation film 3 composed of a polymer material. The insulation film 3 is provided to prevent a bonding wire from coming into contact with another adjacent bonding wire, inner leads and tabs and being short-circuited after it has been bonded.

The insulation film 3 is composed of an electric insulation polymer material composed of aromatic polyester, polyimide, etc. according to the present invention. In this case, the insulation film 3 can be formed in such a manner that the metal core wire is caused to pass through a solution prepared by dissolving the polymer material in solvent and then the solvent is volatilized, the metal core wire is caused to pass through the melted polymer material prepared by heating it and then it is cooled, or the polymer material is sprayed on the surface of the metal core material or monomer, etc. is deposited on the surface of the metal core material and then they are polymerized by being heated or subjected to photochemical polymerization.

On the other hand, the insulation film is preferably an easy-to-flow material so that when the wire is bonded to bonding pads of a pellet, inner leads of a lead frame, or a wire bonding surface such as a metalized surface of a package composed of ceramics or the like, only the insulation film located at a bonding position is decomposed or melted from the surface of the metal core wire and removed by being pushed away.

Relatively brittle polymer materials such as polystyrene and polymethyl methacrylate which are removed by being exfoliated are not preferable, because they cause wire break.

Figure 2:
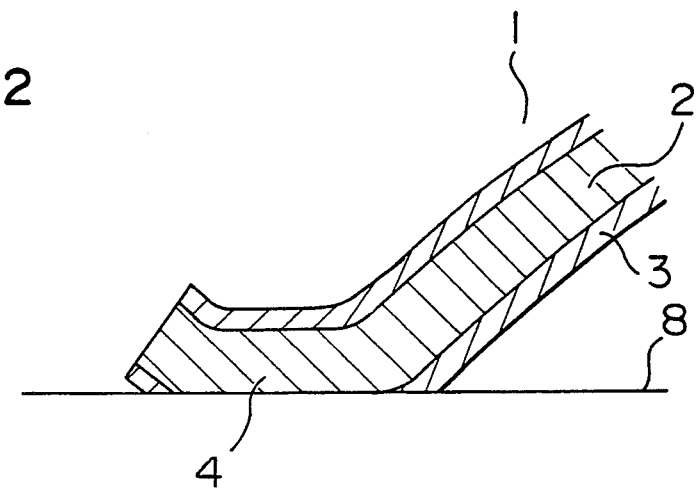
FIG. 2 is a partial cross sectional view showing a state in which an ultrasonic bonding is carried out using a bonding wire according to the present invention.

FIG. 2 shows a state in which the bonding wire 1 is bonded to a lead frame 8, wherein no insulation film 3 is left at a bonded surface, because it is melted there and pushed away to another portion or caused to disappear by being decomposed, whereby bonding can be securely carried out.

Figure 3:
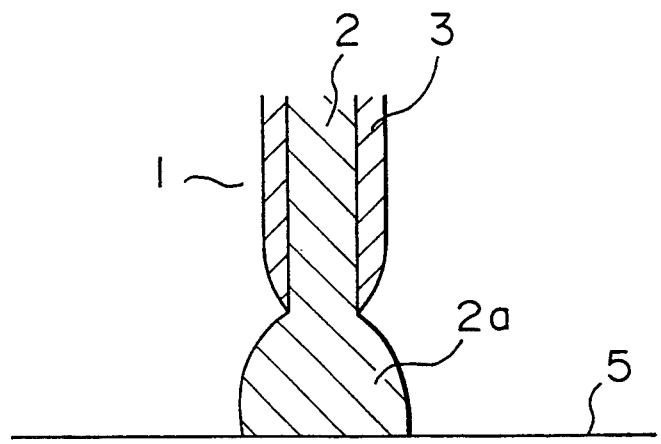
FIG. 3 is a partial cross sectional view showing a state in which a ball bonding is carried out using a bonding wire according to the present invention.

Further, as shown in FIG. 3, when, for example, a bonding wire having a metal core wire composed of gold is ball bonded, bonding can be securely carried out without preventing the ball 2a of the insulation film coated wire 1 from bonding to the wire bonding surface 4 in such a manner that the insulation film 3 is caused to disappear by being melted or decomposed when the ball 2a of the metal core wire 2 is formed, pushed away to another portion, and the like.

This is similarly applicable to a case in which bonding is carried out by forming a ball of aluminum in an inert gas atmosphere.

Therefore, according to the present invention, the insulation film coating the surface of the wires can prevent the occurrence of short-circuiting even if adjacent bonding wires are come into contact each other or a wire comes into contact with inner leads or tabs of an adjacent lead frame after wire bonding has been carried out.

As a result, the bonding wire according to the present invention can be effectively used as a long span wire used for multi-pin.

Further, the wire according to the present invention can carry out a so-called reverse bonding by which the wire is bonded to a lead frame prior to a pellet, and thus enables a package cap to be composed of metal.

Figure 5:
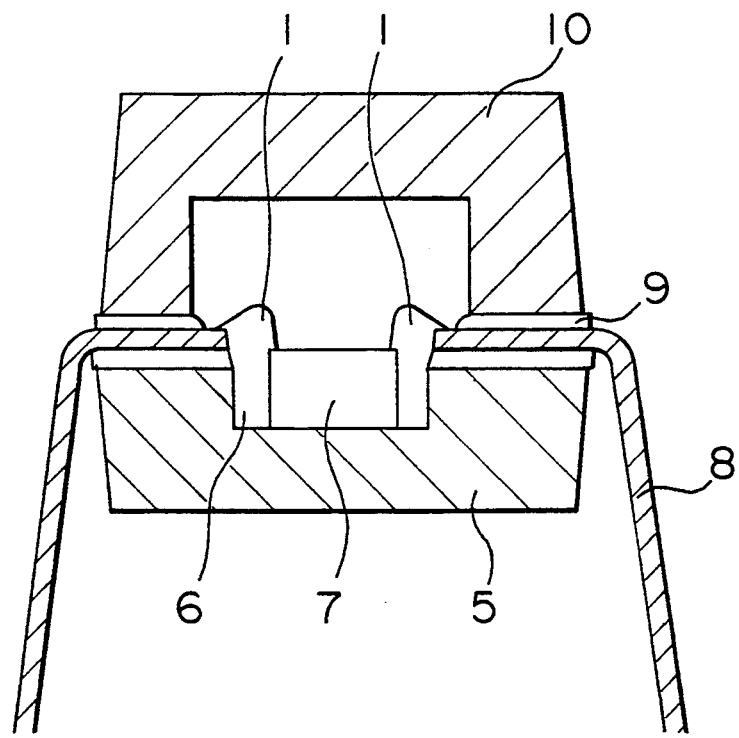
FIG. 5 is a cross sectional view an example of a semi-conductor device to which wire bonding is carried out using a bonding wire according to the present invention.

FIG. 5 is a cross sectional view of an example of a semi-conductor device to which wire bonding is carried out using the wire according to the present invention.

In FIG. 5, as described above, the bonding pads of a semi-conductor pellet 7 mounted in the cavity 16 of a base 5 of a ceramic package are bonded to the inner leads of a lead frame 8 by the bonding wires and electrically connected thereto. In addition, the base 5 is hermetically sealed from a cap 10 by a low melting point glass 9.

In this semi-conductor device, since short-circuiting caused by bonding wires coming into contact each other or a bonding wire coming into contact with adjacent inner leads and the like of a lead frame can be prevented by the insulation film 3 of the polymer material coating the surface of the metal core wire 2 of the bonding wire 1, a span of the bonding wire can be made sufficiently long.

The semi-conductor device according to the present invention can be obtained by bonding respective elements by a usual method using the bonding wire obtained by the present invention.

EXAMPLES

The present invention will be described with reference to examples, but is not of course limited thereto.

First, test methods used in the following examples will be described.

a. Drop Impact Test and Evaluation of the Results thereof

An impact force of 1 cm.g was applied by a falling weight at a room temperature using REA method which is a typical test method to the casing of an electric wire and cable, and whether crack was developed on a surface resin or not was confirmed by a scanning type electron microscope (SEM) (magnification: 700). Examples to which no crack was developed were marked ○ and examples to which crack was developed were marked X.

b. Melt Index

Extrusion was effected at an extrusion temperature of 300° C. with a load of 2.160 Kg based on ASTM-D1238.

c. Evaluation of Continuous Bonding Property of Bonding Wire and Insulation Film With respect to a continuous bonding property of a bonding wire with a lead frame, wires continuously bonded 2000 times or more were marked ○ and wires cut off before they were continuously bonded 2000 times were marked X. The quality of an insulation film was observed by a scanning type electron microscope (SEM) at a magnification of about 1000, and an insulation film having a uniform quality was marked ○ and an insulation film causing exfoliation or having an irregular thickness was marked X.

EXAMPLE 1-3

As a method of forming an insulation film, a bonding wire as a metal core wire composed of high purity gold having an outside diameter of 30 μm was caused to pass through a solution prepared by dissolving aromatic polyester resin having the above basic skeleton in chloroform, lifted in the vertical direction, and solvent was removed therefrom to thereby make a bonding wire coated with the insulating aromatic polyester resin.

As a polymer resin material of the aromatic polyester resin, aromatic polyesters composed of copolymer of bisphenol-A and dicarboxylic acid (a mixing ratio of terephthalic acid and isophthalic acid: 1:1) having a predetermined melt index value were synthesized, respectively, according to a usual interfacial polycondensation method [Shin Jiken Kagaku Koza Vol. 19, polymer Chemistry (I), p. 149 by Japan Chemical Association] and used for Examples 1 to 3 and Comparative Examples 1 and 2.

Since a thickness of a coating film depends upon concentration and viscosity of the solution and a coating speed as well as a melt index, the concentration of the solution and the coating speed were adjusted in accordance with the melt index of the aromatic polyester resins used so that respective covering films have a thickness of about 0.3 μm.

Coating films were formed on the bonding wires using a chloroform solution of aromatic polyester resins having a melt index of 3.5, 13, 55 g/10 min, respectively so that insulation bonding wires having a coating film thickness of 0.3 μm were made.

Table 1 shows the results of a continuous bonding test and a drop impact test effected using the coated bonding wires. They were observed by an SEM and all of them were confirmed to be smoothly coated.

Comparative Example 1

Although the bonding wires were tried to be coated with a chloroform solution of aromatic polyester resin having a melt index of 0.8 g/10 min, a coating layer having uniform thickness could not be formed.

When they were observed using an SEM, it was found that the thickness of the coating layer in the lengthwise direction of the bonding wires had dispersion about twice a large thickness. In addition, a very small number of the insulated bonding wires having a relatively uniform covering thickness of 0.3 μm obtained from the thus made coated bonding wires were tried to be bonded to a lead frame, but the bonding property thereof with the lead frame was very poor, as shown in Table 1, and thus they were not suitable for practical use.

EXAMPLE 2

A coating film was formed to bonding wires using a chloroform solution of an aromatic polyester resin having a melt index of 120 g/10 min so that it had a thickness of 0.3 μm. The thus made coated bonding wires were observed by an SEM and it was found that the resin was easily exfoliated from the surface of the wires and the wires were not securely insulated, and thus they were not suitable for practical use, although no problem arose in bonding.

It is supposed that when a melt index is too large, i.e., a molecular weight is too small, perhaps, a coating film may be poorly adhered to a wire and liable to be exfoliated.

TABLE 1

|  | Example 1 | Example 2 | Example 3 | Comparative Example 1 | Comparative Example 2 |
| --- | --- | --- | --- | --- | --- |
| Melt Index (g/10 min) | 3.5 | 13 | 55 | 0.8 | 120 |
| Continuous Bonding Property | ○ | ○ | ○ | X | ○ |

TABLE 1-continued

|  | Example 1 | Example 2 | Example 3 | Comparative Example 1 | Comparative Example 2 |
|---|---|---|---|---|---|
| Outside Appearance of Coating Film | ◯ | ◯ | ◯ | X | X |
| Drop Impact Test | ◯ | ◯ | ◯ | ◯ | X |

As apparent from Table 1, when the melt index was too large, the formation of the coating layer having uniform thickness was difficult, and even if it was formed, the bonding wire was poorly bonded to the lead frame, and when the melt index was too small, the coating film was poorly bonded to the wire and liable to be exfoliated and thus both the cases were not suitable for practical use.

EXAMPLES 4–12

Comparative Examples 3–6

As a polymer resin material, U Polymer 100 of Unitica Colo., Ltd. as polyarylate (an aromatic polyester), ULTEM of Mitsui Toatsu Kagaku Co., Ltd. as polyimide, VICTREX of Sumitomo Kagaku Co., Ltd. as polyether ether ketone, NOVAMID of Mitsubishi Kasei Co., Ltd. as polyamide, polyester sulfone (VICTREX) or ICI Japan Co., Ltd. as polysulfone, polyester carbonate of Shin Nihon Seitetsu Co., Ltd. as liquid crystal polymer; and as a comparative resin material, Estyrene G15 of Shin Nihon Seitetsu Kagaku Co., Ltd. as polystyrene and Parapet of Kyowa Gasu Kagaku Co., Ltd. as polymethyl methacrylate were dissolved in solvent. Then, they were adjusted to provide bonding wires to which a coating film having a thickness of 0.5 μm was coated through the same treatment as in Examples 1 to 3. The wires were subjected to a bonding property test and like. Tables 2 and 3 show the results of the tests.

As also apparent from Examples 4 to 8 and Comparative Examples 3 to 4, the examples to which no crack was developed in the drop weight test could be continuously bonded, whereas the examples to which crack was developed in the drop weight test were cut off and thus could not be continuously bonded.

Further, to examine the effect caused by a thickness of the insulation coating film, a continuous bonding and insulating properties were tested using insulation film coated wires having a different thickness by changing a concentration of a shcloroform solution, a take-up speed and the like, the coating film being made using U Polymer 100 of Unitica Colo., Ltd. used in Example 4.

The insulation test was effected based on JIS C 3005-1986, Item 1 and the examples which were insulated in air at a room temperature when a voltage of at least 15 V was applied thereto were marked ◯ and the examples other than the above were marked X.

TABLE 4

|  | Example 10 | Example 11 | Example 12 | Comparative Example 5 | Comparative Example 6 |
|---|---|---|---|---|---|
| Thickness of Coated Film μm | 0.05 | 0.5 | 1.2 | 0.005 | 11 |
| Bonding Property | >12000 | >12000 | >2000 | >12000 | <20 |
| Insulating Property | ◯ | ◯ | ◯ | X | ◯ |
| Drop Impact Test | ◯ | ◯ | ◯ | X | ◯ |

EXAMPLE 13

Figure 4:
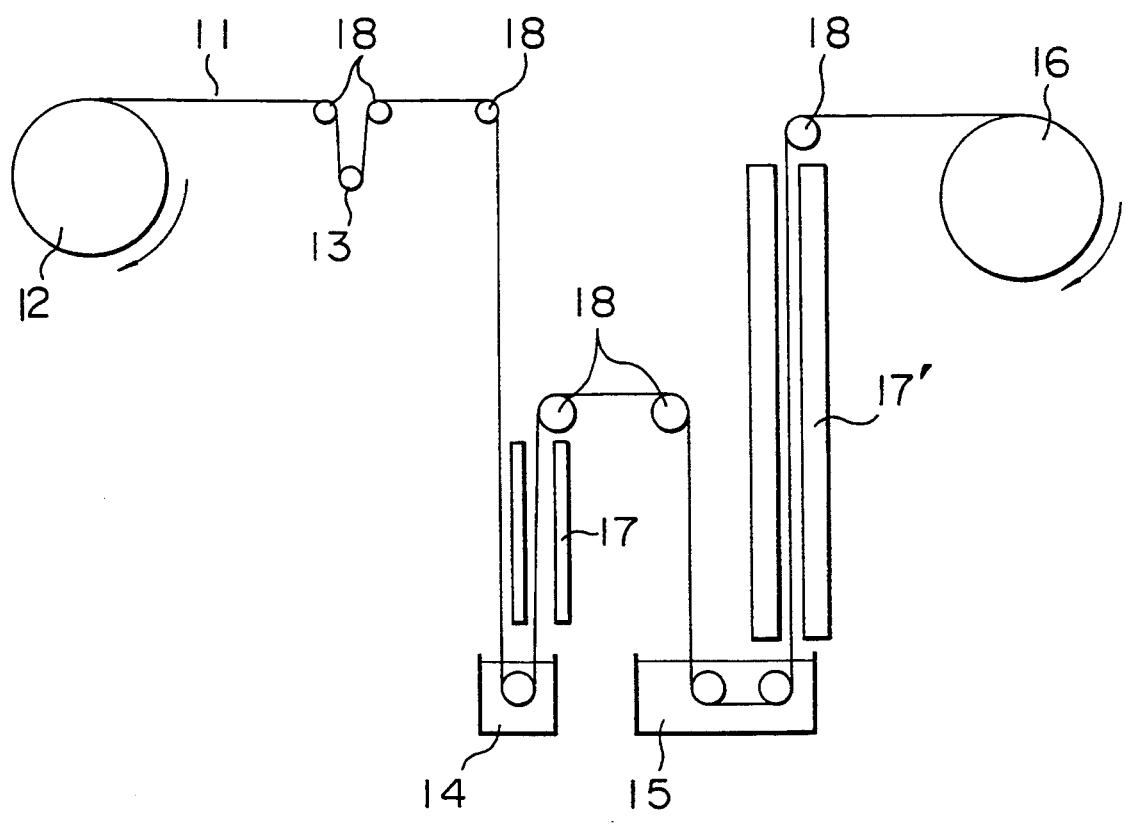
FIG. 4 is a schematic diagram showing an example of an apparatus embodying the present invention.

FIG. 4 shows an example of an apparatus embodying the present invention, wherein 11 designates a bonding wire, 12 designates a feed spool for feeding the bonding wire, 13 designates a back tension controller for detecting tension applied to the bonding wire and controlling a feed speed, 14 designates a pretreatment bath also effecting cleaning, 15 designates a resin coating unit, 16 designates a take-up spool, 17 and 17' designate drying furnaces, and 18 designates a guide roller for guiding the bonding wire.

TABLE 2

|  | Example 4 | Example 5 | Example 6 | Example 7 | Example 8 | Example 9 |
|---|---|---|---|---|---|---|
| Resin Material | Polyarylate | Polyimide | Polyether-Ether Ketone | Polyamide | Polysulfone | Liquid Crystal Polymer |
| No. of Continuations | >1200 | >2000 | >2000 | >2000 | >2000 | >2000 |
| Drop Impact Test | ◯ | ◯ | ◯ | ◯ | ◯ | ◯ |

TABLE 3

|  | Comparative Example 3 | Comparative Example 4 |
|---|---|---|
| Resin Material | Polystyrene | Polymethyl Methacrylate |
| No. of Continuations | <30 | <50 |
| Drop Impact Test | X | X |

As an example of the present invention, a resin film coated insulation bonding wire having satisfactory characteristics can be made by the following process.

After being sufficiently cleaned, the bonding wire 11 is mounted on the feed spool 12, continuously fed therefrom by the rotation of the take-up spool 16, further cleaned by chloroform in the pretreatment bath 14, and caused to pass through the drying furnace 17 to remove solvent.

The above pretreated bonding wire 11 is caused to pass through the coating unit 15 containing a coating solution which is prepared in such a manner that resin is dissolved and filtrated through a filter of 0.2 μm mesh, then drawn upward in the vertical direction and the solvent thereof is removed while the bonding wire 11 is caused to pass through the drying furnace 17', whereby the bonding wire coated by the insulation resin is formed and wound by the take-up spool 16.

When a two-stage drying furnace, which at first gradually dries the bonding wire 11 at a low temperature (30° to 45° C.) and next dries the same at about the boiling temperature of chloroform (55° to 65° C.), is used as the drying furnace 17', the insulation film having a preferable surface property can be obtained.

The surface of the resin film coated bonding wire is subjected to an electrostatic charge prevention treatment by an ionized air shower, and then re-wound by designated spools to a designated length. The back tension controller applies a predetermined tension (about 3 g) to the wire bonding to check whether the wire is cut off while it is coated with the film, and prevents it from being expanded by an excessive tension applied thereto or from being out of the guide roller because a tension applied thereto is too small.

A gold bonding wire having a diameter of about 30 μm was used as the bonding wire. Used as the resin was U Polymer, grade U100 of Unitica Colo., Ltd. which was dissolved in chloroform and filtrated through a filter of 0.2 μm mesh.

The insulation resin film was arranged to have a thickness of 0.5 μm in such a manner that a concentration of the resin solution was adjusted to 5 wt % and the film was wound at a speed of 3.4 m/min.

When an insulation film coated wire having a film thickness of 0.5 μm of the thus made bonding wires was used for wiring a semi-conductor device, no electric short-circuiting was caused and a good continuous bonding property was obtained.

INDUSTRIAL APPLICABILITY

According to the present invention, a polymer resin film coated insulation bonding wire obtained by using a particular polymer resin material and coating it with an insulation layer having a uniform and particular thickness is excellent in an insulating property, continuous bonding property, heat resistance and the like and thus preferably used in semi-conductor devices.

Further, semi-conductor devices using the bonding wire according to the present invention have such advantage that they are highly reliable and can be continuously manufactured.

According to the manufacturing method of the present invention, resin film coated insulation bonding wires can be continuously and effectively manufactured, the bonding wires being used for wiring semi-conductor devices and having no possibility of arising electric short-circuiting caused when adjacent bonding wires are come into contact each other or a bonding wire comes into contact with an adjacent lead frame, tabs or other conductors.

Further, when the coating apparatus according to the present invention is disposed as a part of a wire drawing process, wire drawing and coating can be continuously carried out easily.

Further, a coating bath can be also made to a multilayer by disposing the coating apparatus in multistage in the lengthwise direction of the bonding wire.

What is claimed is:

1. An insulation film covered bonding wire, comprising a conductive metal core wire the circumference of which is coated with an insulation film comprised of an at least one polymer resin material selected from a group of aromatic polyesters, polyether-ether ketones, polyamides, polysulfones, and liquid crystal polymers, wherein no crack is developed to said resin material when an impact of 1 cm.g is applied to wire coated with said resin material by a falling weight;

wherein said insulation film comprised of said polymer resin material has a melt index of 1.0 to 100 g/10 min; and, wherein said insulation film comprised of said polymer resin material has a thickness of 0.01 to 10 μm.

2. An insulation film coated bonding wire according to claim 1, wherein said polymer resin material is a substance produced by the reaction of an aromatic dihydroxy compound with an aromatic dicarboxylic acid.

3. An insulation film coated bonding wire, wherein the polymer resin material according to claim 2 has the following formula as the basic skeleton thereof

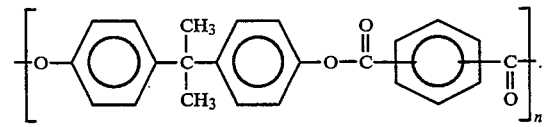

4. An insulation film coated bonding wire according to claim 1, wherein said insulation film comprised of said polymer resin material has a thickness of 0.01 to 2 μm.

5. An insulation film coated bonding wire according to claim 1, wherein said insulation film comprised of said polymer resin material has a thickness of 0.02 to 1 μm.

6. A semi-conductor device, comprising a semi-conductor pellet having bonding pads electrically connected to conductors to external output terminals wherein the bonding wire according to claim 1 is used for electrical bonding.

* * * * *